United States Patent
Katsurada et al.

[11] Patent Number: 5,865,726
[45] Date of Patent: Feb. 2, 1999

[54] FRONT END STRUCTURE OF SIDE-VIEW TYPE ENDOSCOPE

[75] Inventors: Hiroyuki Katsurada; Shinichi Matsuno, both of Tokyo, Japan

[73] Assignee: Asahi Kogaku Kogyo Kabushiki Kaisha, Tokyo, Japan

[21] Appl. No.: 824,168

[22] Filed: Mar. 26, 1997

[30] Foreign Application Priority Data

| Mar. 27, 1996 | [JP] | Japan | 8-071598 |
| Mar. 27, 1996 | [JP] | Japan | 8-071599 |
| Apr. 10, 1996 | [JP] | Japan | 8-088033 |
| Jan. 16, 1997 | [JP] | Japan | 9-005421 |
| Jan. 16, 1997 | [JP] | Japan | 9-005423 |

[51] Int. Cl.$^6$ ........................................ A61B 1/04
[52] U.S. Cl. ........................ 600/127; 600/121; 600/129
[58] Field of Search ........................ 600/104, 106, 600/107, 113, 121, 123, 127, 129, 128, 160, 170, 171

[56] References Cited

FOREIGN PATENT DOCUMENTS 62-6716  1/1987  Japan .
4-51764  12/1992  Japan .

*Primary Examiner*—Beverly M. Flanagan
*Attorney, Agent, or Firm*—Kane,Dalsimer,Sullivan, Kurucz, Levy, Eisele and Richard, LLP

[57] ABSTRACT

A front end structure of a side-view type endoscope includes a metal front end body on the side face of which a view window is provided, and an end cap of a resilient material in the form of a cylinder with a closed bottom. The end cap is detachably attached to the front end body and is provided with an opening through which at least the view window is exposed. Detachment preventing engagement portions are provided between the end cap and the front end body on opposite sides of the view window. The detachment preventing engagement portions are each provided with at least one recess and at least one projection which is engaged in the recess to resist the movement of the end cap in the end cap detachment direction.

7 Claims, 15 Drawing Sheets

PRIOR ART

FRONT END STRUCTURE OF SIDE-VIEW TYPE ENDOSCOPE

BACKGROUND OF THE INVENTION

1. Field of the Invention

The present invention relates to a structure of a front end of a side-view type endoscope on the side surface of which a view window is provided.

2. Description of the Related Art

FIGS. 12 and 13 show a perspective view and a sectional side view of a front end portion of a known side-view type endoscope, respectively.

A front end body 1 provided at the front end of an insertion portion of an endoscope is made of corrosion resistant metal such as stainless steel and a view window 4, an illumination window 5, and a treatment tool insertion opening through which a treatment tool extends are provided on the side surface thereof.

A front end cap 30 which is made of an elastic material such as fluoro-rubber is in the form of a cylinder with a closed bottom and is provided with an opening 31 corresponding to the view window 4, the illumination window 5, and the opening 6.

The end cap 30 is detachably attached to the front end body 1. The end cap 30 is detached from the front end body 1 in FIG. 12 and is attached to the front end body 1 in FIG. 13.

When the front end body 1 is capped with the end cap 30, a peripheral projection 32 provided on the inner peripheral surface of the end cap 30 at the rear end thereof is fitted in a peripheral groove 7 formed on the outer peripheral surface of the rear end of the front end body 1.

The front end body 1 is provided on the front end surface thereof with a stepped portion 1a against which the end cap 3 abuts to prevent the end cap 30 from rotating relative to the front end body 1.

To detach the end cap 30 from the front end body 1, the portion of the insertion portion of the endoscope that is located adjacent to the rear end of the front end body 1 and the front end portion of the end cap 30 are held by the fingertips, respectively, as shown in FIG. 14. Then the end cap 30 is pulled forward and moved downward to disengage the same from the stepped portion 1a, as indicated by an arrow "A", so that the end cap 30 is partly detached from the front end body 1. In this state, the end cap 30 is pulled further forward, the end cap 30 is completely detached from the front end body 1, as shown in FIG. 15.

However, in the detachment operation, there is a stress concentration at the corner portions of the rear end of the opening 31. Consequently, there is a possibility that cracks 100 may occur in the rear corner portions of the opening 31 when the attachment and detachment of the end cap 1 to and from the front end body 1 are repeatedly performed. The same would be true when the front end of the insertion portion is moved while the front end of the end cap 30 is pressed hard against a mucous membrane in the body cavity of a patient.

If the cracks 100 are produced, the end cap 30 can be partly or completely detached from the front end body 1 within the body cavity of a patient during an examination using the endoscope. Consequently, the front end body 1 which is made of metal is exposed, so that the mucous membrane can be injured by the exposed front end body 1.

SUMMARY OF THE INVENTION

It is an object of the present invention to provide a safe front end structure for a side-view type endoscope wherein no accidental partial or complete detachment of an end cap from the front end body takes place, and wherein if a crack occurs in the front end cap, no detachment of the end cap from the front end body tends to occur, thus resulting in little or no injury to the mucous membrane.

To achieve the object mentioned above, according to the present invention, there is provided a front end structure of a side-view type endoscope, including a metal front end body on the side face of which a view window is provided, and an end cap of a resilient material in the form of a cylinder with a closed bottom, said end cap being detachably attached to the front end body and being provided with an opening through which at least the view window is exposed, wherein the improvement comprises detachment preventing engagement portions provided between the end cap and the front end body on opposite sides of the view window, said detachment preventing engagement portions each being provided with at least one recess and at least one projection which is engaged in the recess to resist the movement of the end cap in the detachment direction in which the end cap is detached from the front end body.

The detachment preventing engagement portion provided on the rear side of the view window is comprised of an is annular groove formed in the front end body and an annular projection provided on the end cap.

The front end body is provided with a planar on which the view window is formed. The detachment preventing engagement portion provided on the rear side of the view window is located between the planar portion of the front end body and the end cap, while the detachment preventing engagement portion provided on the front side of the view window is located between the front end face of the front end body and the front bottom face of the cylindrical end cap.

At least one of the above-mentioned detachment preventing engagement portions is provided with a means for preventing the rotation of the end cap.

A second aspect of the invention comprises a front end body made from a rigid circular rod, a planar portion which is formed by partly cutting away a portion of the rod other than the rear end and is provided with a view window, an illumination window, and a rectangular treatment tool insertion opening.

The end cap is provided with an opening located outside the planar portion. The size of the opening is minimized so as not to interfere with the functions of the view window, illumination window, and the treatment tool insertion opening of the front end body.

The second aspect of the invention further comprises a treatment tool raising piece which is provided in the treatment tool insertion opening so as to move in accordance with a remote-control operation. The opening of the end cap is made as small as possible so as not to interfere with the treatment tool raising piece.

The minimizing of the size of the end cap opening does not reduce the field of view of the endoscope or the emission angle of illumination light emitted from the illumination window.

The opening of the end cap is defined by seven rectilinear portions. The first and second portions extend along the side edges of the rectangular treatment tool insertion opening. The third portion extends parallel to the longitudinal direction of the treatment tool insertion opening, and is located as close to the view window and illumination window as possible, in the circumferential direction of the end cap. The fourth and fifth rectilinear portions extend along the front and rear side edges of the treatment tool insertion opening.

The sixth and seventh portions extend along the circumferential direction of the end cap, and connect the second and third portions with the view window and the illumination window being exposed.

The first to third rectilinear portions and the fourth to seventh portions are normal to each other, and their intersections are smoothly connected by arcs. The difference between the fourth and fifth portions is larger than the difference between the sixth and seventh portions.

In the third aspect of the invention, the outer edge of the end cap that is overlapped on a boundary between the circular rod portion of the front end body and the planar portion is smoothly rounded without having an angled portion. The rear right and left corner portions of the opening of the end cap are also smoothly rounded without having angled portions.

The front end body is further comprised of a recess at the rear end of the planar portion on which the view window is formed, and an engagement projection which is engaged in the recess. The contour of the opposite sides of the opening at the rear end of the end cap is located more outward than the contour of the portion of the end cap where the engagement projection is located, when viewed in the direction parallel with the planar portion. The contour of the opposite sides of the opening at the rear end of the end cap is also located more outward than the surface of the view window formed on the planar position.

The present disclosure relates to subject matter contained in Japanese Patent Application Nos. 8-71598 (filed on Mar. 27, 1996), 8-71599 (filed on Mar. 27, 1996), 8-88033 (filed on Apr. 10, 1996), 9-5421 (filed on Jan. 16, 1997) and 9-5423 (filed on Jan. 16, 1997) which are expressly incorporated herein by reference in their entireties.

BRIEF DESCRIPTION OF THE DRAWINGS

The invention will be discussed below in detail with reference to the accompanying drawings, in which.

DESCRIPTION OF THE PREFERRED EMBODIMENT

Figure 1:
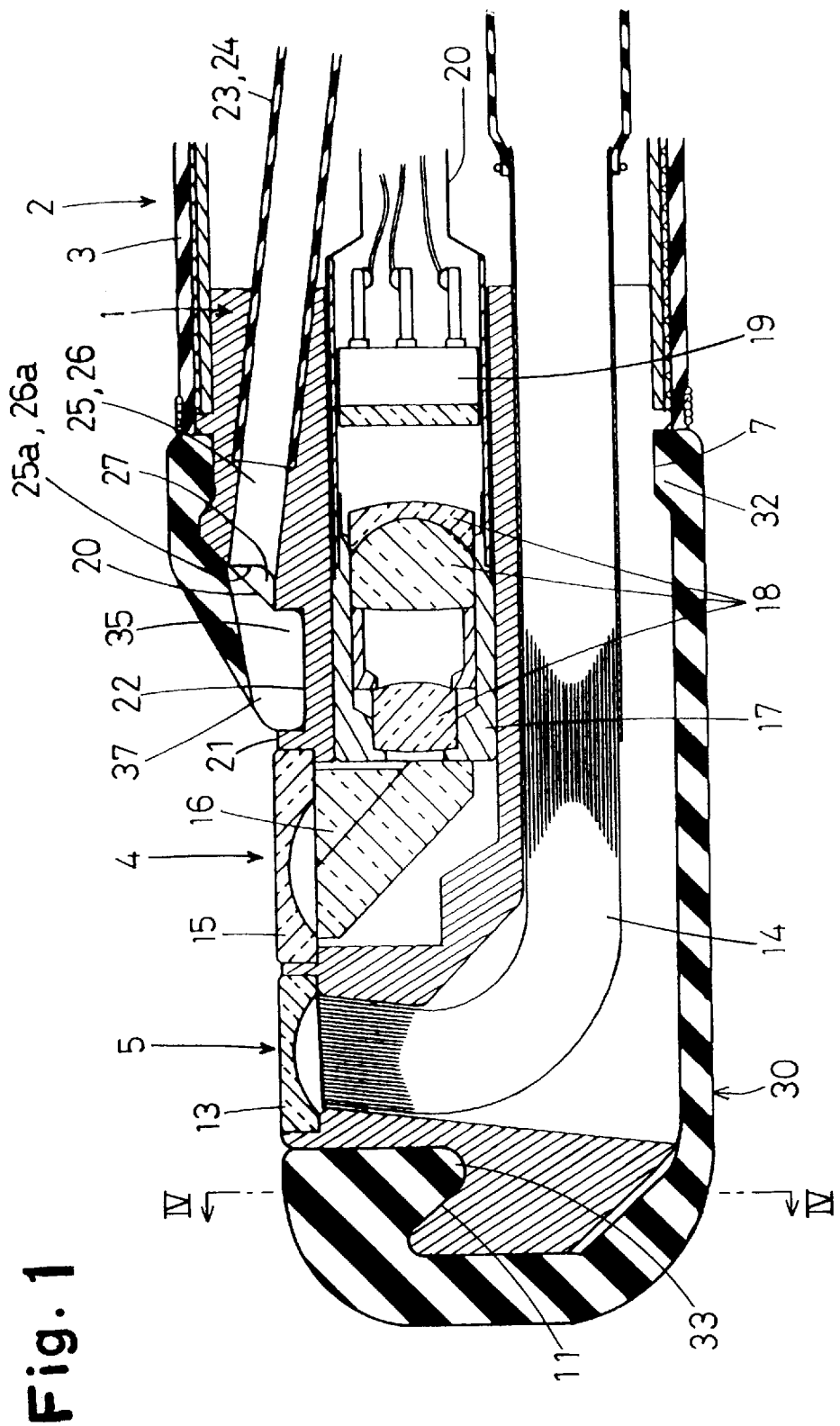
FIG. 1 is a sectional view of a side-view type endoscope according to an embodiment of the present invention, taken along the line I—I in FIG. 2.
Figure 2:
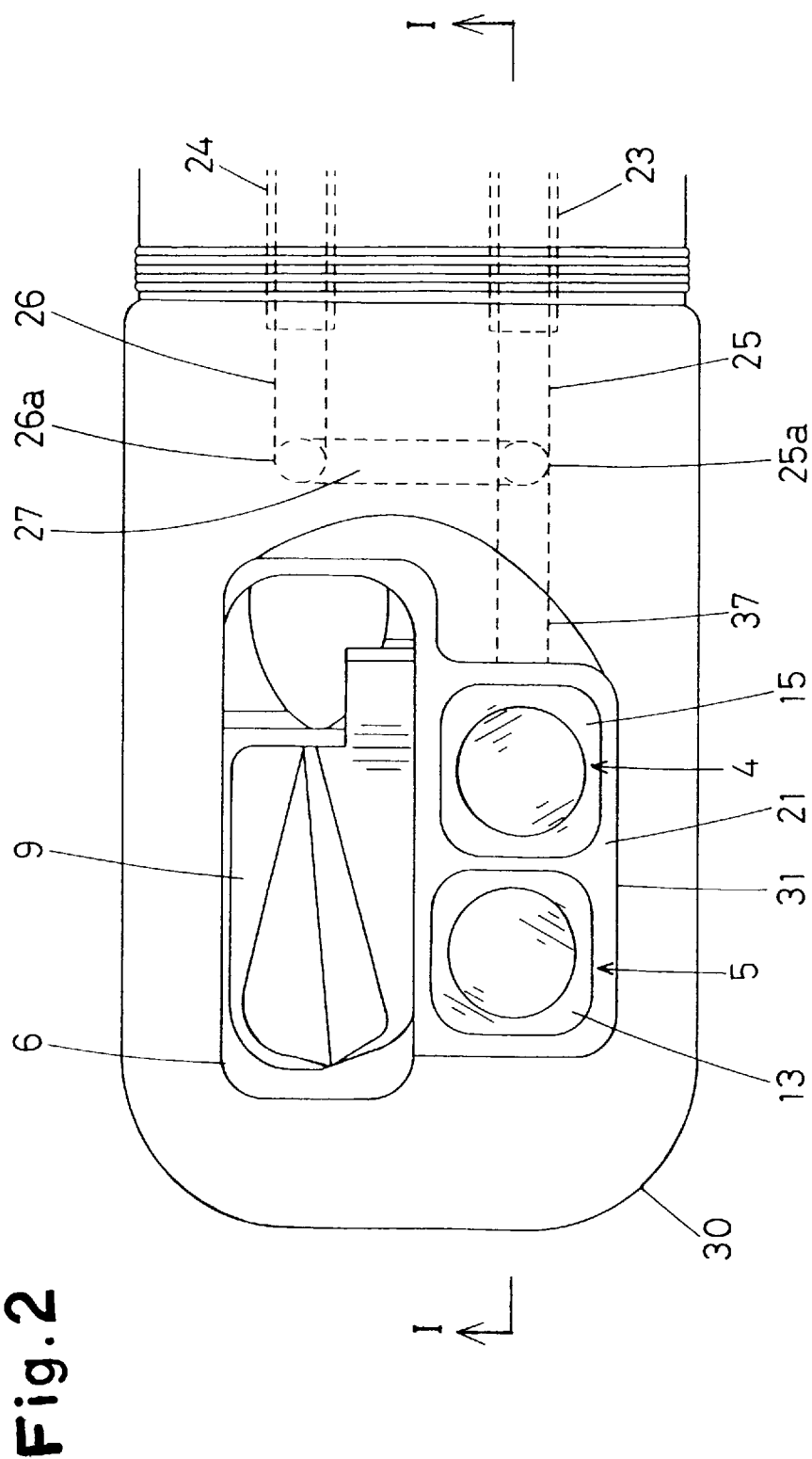
FIG. 2 is a plan view of FIG. 1.

FIGS. 1 through 4 show a first embodiment of the present invention. A front end body 1 which is made of a corrosion resistant metal such as stainless steel is connected to the front end of a flexural portion 2 provided at the front end of a flexible insertion portion of the endoscope. The flexural portion 2 is covered by a flexible rubber tube 3.

The front end body 1 is in the form of a circular rod whose side surface is partially cut to form a flat surface (planar portion) 21 on which the view window 4, the illumination window 5 and the treatment tool insertion opening 6 are provided.

The front end body 1 is capped airtight with the end cap 30 made of an elastic material such as fluororubber so that the portions of the front end body other than the view window 4, the illumination window 5 and the opening 6 are not exposed.

Figure 3:
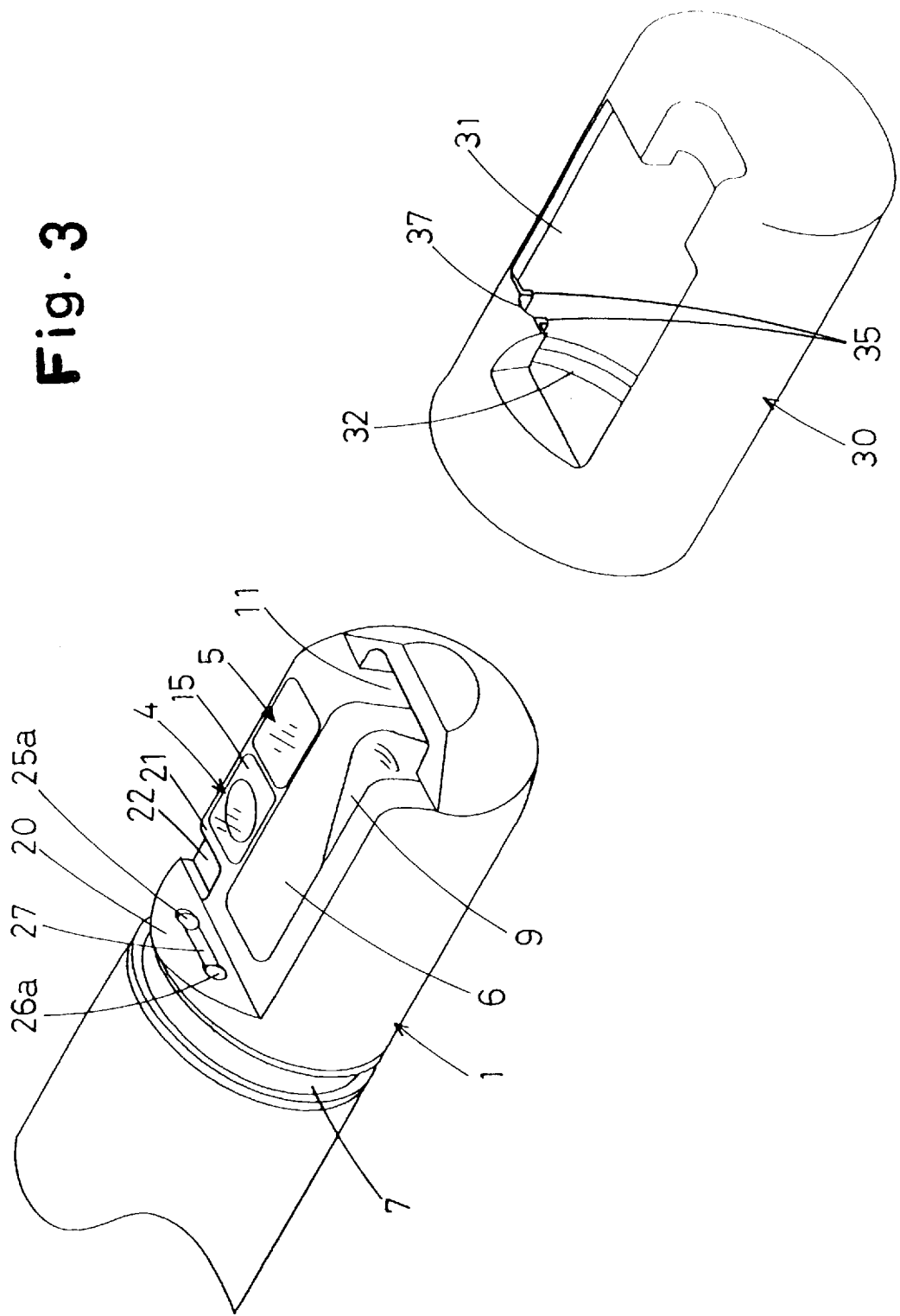
FIG. 3 is a perspective view of the side-view type endoscope shown in FIGS. 1 and 2, in which an end cap is detached from a front end body.

The end cap 30 is in the form of a cylinder with a closed bottom, i.e., a cylinder having a closed front end and an open rear end. The end cap 30 is detachably attached to the front end body 1, as shown in FIG. 3. The end cap 30 is provided with an opening 31 corresponding to the view window 4, the illumination window 5, and the opening 6 formed on the planar portion 21 of the front end body 1.

A treatment tool raising piece 9 is rotatably or swingably supported in the opening 6. The raising piece 9 swings or rotates in accordance with a remote-control operation. The front end of a treatment tool insertion channel (not shown) opens into the opening 6 in the rear of the raising piece 9.

As can be seen in FIG. 1, the illumination window 5 is provided with light distribution lens 13 which is made of a concave lens to increase the emission angle of illumination light. The front (outer) surface of the light distribution lens 13 is substantially flush with the planar portion 21. The emission end of an illumination light guiding fiber bundle 14 is opposite the light distribution lens 13.

The view window 4 is provided with a cover lens 15 of a viewing optical system which is substantially flush with the planar portion 21. There is a prism 16 inside the cover lens 15 to bend (reflect) the optical axis of the viewing optical system. An objective lens group 18 held by a lens frame 17 is provided behind the prism 16.

An image receiving surface of a solid-state image pickup device 19 which is comprised of, for example, a charge-coupled device (CCD) is provided at an image forming plane on which an object image is formed by the objective lens group 18. The solid-state image pickup device 19 is connected to signal cables 20 extending backward.

The planar portion 21 of the front end body 1 lies in conjugation with the rear end of the cover lens 15 of the view window 4. The planar portion 21 is provided on the rear end thereof with a generally rectangular recessed groove 22.

The end cap 30 is provided with a projection 35 which can be fitted in the recessed groove 22 of the front end body 1 to form a liquid-tight seal. When the projection 35 is fitted in the recessed groove 22, no rotation of the end cap 30 relative to the front end body 1 takes place. The recess 22 and the projection 35 constitute a first detachment/rotation preventing engagement portion behind the view window 4.

The planar portion (flat surface portion) 21 of the front end body 1 is connected to an oblique surface 20 into which an air supply passage 25 and a water supply passage 26 open at their front ends. The air supply passage 25 and the water supply passage 26 are connected to an air supply pipe 23 and a water supply pipe 24, respectively.

The air supply passage 25 and the water supply passage 26 are connected by means of an elongated connecting groove 27 which is laterally recessed in the oblique surface 20 of the front end body 1. The air supply passage 25 and the water supply passage 26 open into the connecting groove 27 at the respective outlet ports 25a and 26a.

The end cap 30 is provided, on the portion that contacts with the planar portion 21, with a nozzle 37 which opens toward the surface of the cover lens 15.

The connecting groove 27 formed in the front end body 1 is directly connected to the rear opening of the nozzle 37. Consequently, the air or water supplied through the air supply pipe 23 or the water supply pipe 24 is ejected onto the surface of the cover lens 15 from the nozzle 37 through the connecting groove 27.

An annular projection 32 is provided on the inner peripheral surface of the end cap 30, near the open end of the end cap. A peripheral circular groove 7 is provided on the outer peripheral surface of the front end body, behind the planar portion 21. The annular groove 7 and the annular projection 32 constitute a second detachment preventing engagement portion behind the view window 4.

The end cap 30 is expanded when it is being attached to the front end of the front end body 1. When the peripheral projection 32 is fitted in the peripheral groove 7, the end cap 30 is firmly connected to the front end body 1 so as not to be accidentally detached.

Moreover, the front end body 1 is provided with a recess 11 whose section when viewed in the lateral direction is generally V-shaped, and a projection 33 which can be fitted in the recess 11 is provided on the inner peripheral surface of the front bottom end of the end cap 30, as shown in FIGS. 1 and 3. The recess 11 and the projection 33 constitute a third detachment preventing engagement portion before the view window 4 (i.e., the first front detachment preventing engagement portion).

Thus, when the end cap 30 is attached to the front end body 1, the projection 33 of the end cap 30 abuts against the front end surface of the front end body 1 immediately before the end cap 30 is completely attached to the front end body 1. To fit the projection 33 in the recess 11, it is necessary to raise and deform the projection 33 by applying external force to thereby cause the projection 33 to ride over the front bank portion of the recess 11.

Therefore, when the end cap 30 is completely attached to the front end body 1, the operator can feel a click which is produced when the projection 33 is fitted in the recess 11. Thus, the operator can easily confirm that the end cap 30 is correctly attached to the front end body 1.

Figure 4:
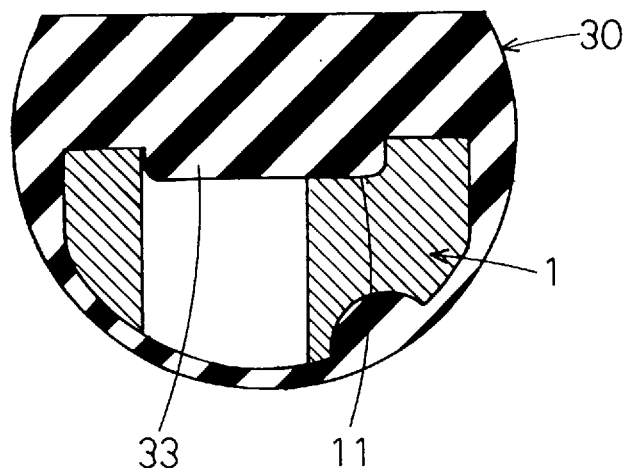
FIG. 4 is a sectional view taken along the line IV—IV in FIG. 1.
Figure 5:
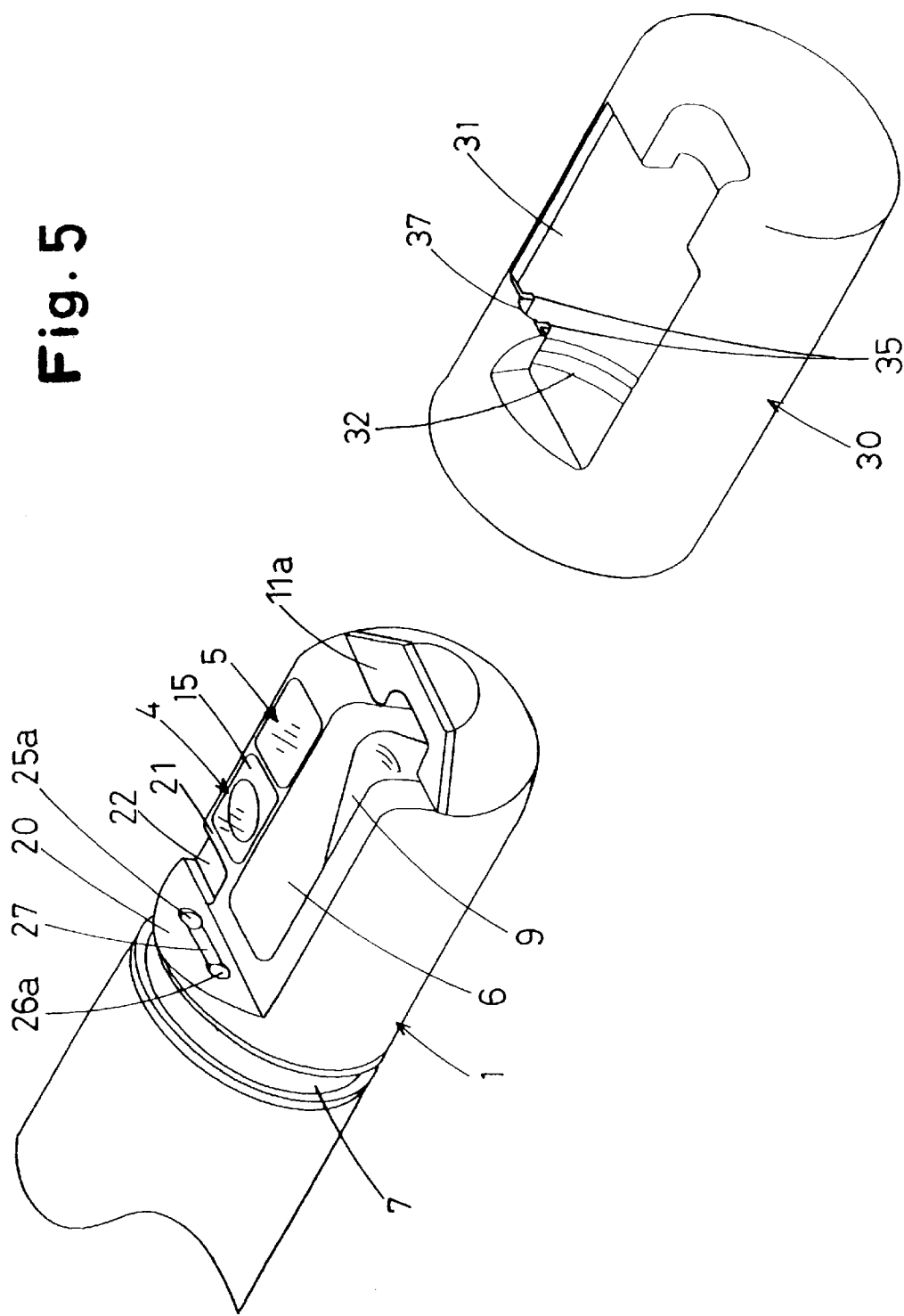
FIG. 5 is a perspective view of a side-view type endoscope in which an end cap is detached from a front end body, according to another embodiment of the present invention.
Figure 6:
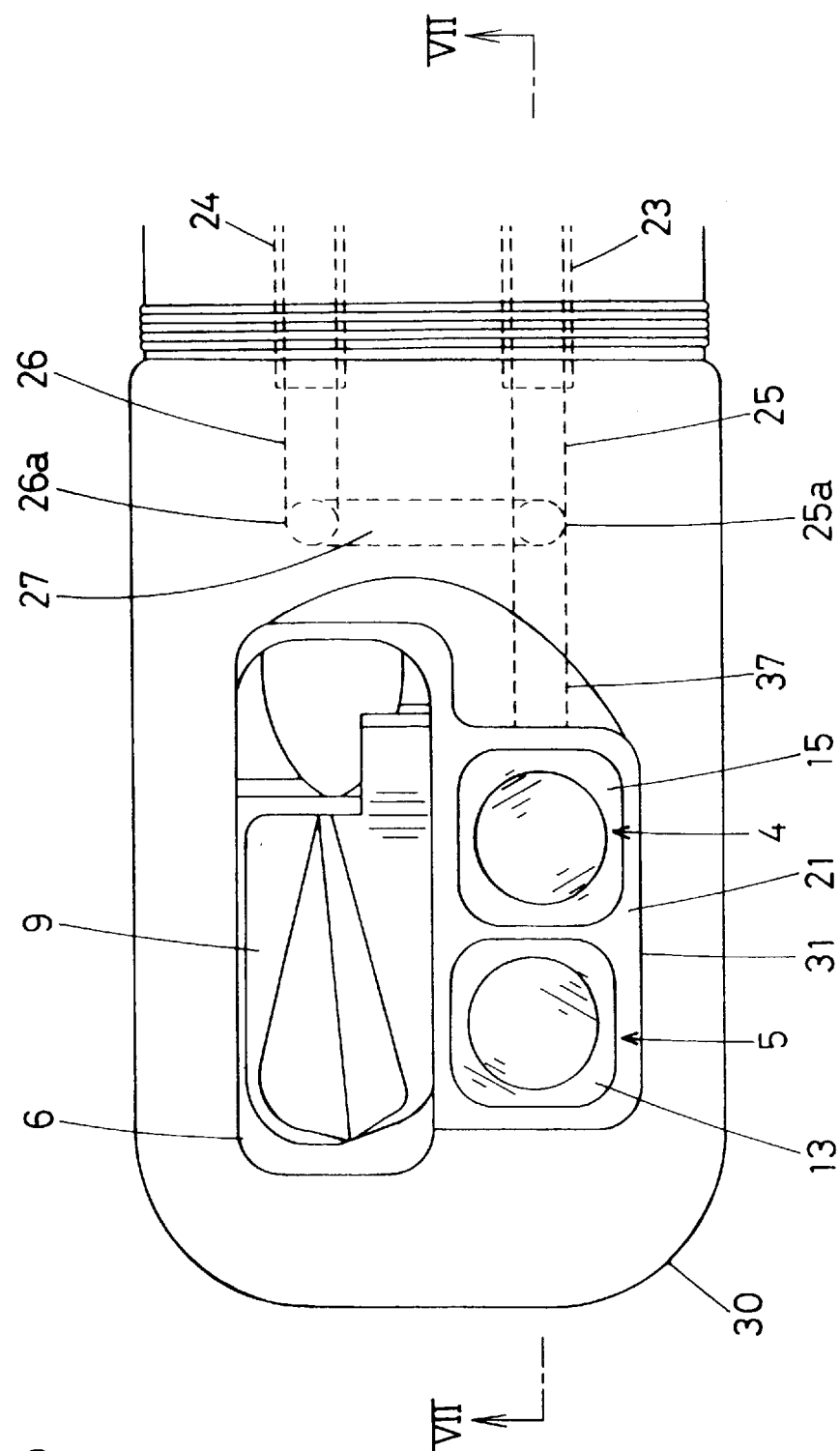
FIG. 6 is a plan view of an end cap attached to the front end body shown in FIG. 5.

As may be seen in FIGS. 1 and 4, once the projection 33 is fitted in the recess 11, the engagement is firmly maintained, and hence, the relative position of the end cap 30 to the front end body 1 can be kept. Consequently, if the end cap 30 is repeatedly attached to or detached from the front end body 1, or the front end of the insertion portion of the endoscope is moved while the front end of the end cap 30 is strongly pressed against a mucous membrane in the body cavity during an examination using the endoscope, no accidental partial or complete detachment of the end cap 30 from the front end body 1 occurs. Moreover, if the end cap 30 is cracked, no accidental detachment of the end cap 30 from the front end body 1 tends to take place, thus resulting in little or no injury to the mucous membrane in the body cavity.

To detach the end cap 30 from the front end body 1, the operation opposite to that for the attachment of the end cap 30 to the front end body 1 is carried out. Namely, the end cap 30 is slid in the direction opposite to the sliding movement upon the attachment of the end cap while elastically deforming the same.

The present invention is not limited to the above-mentioned embodiment. For example, the projection 33 and the recess 11 can be provided on the front end body 1 and the end cap 30, respectively.

According to the embodiment mentioned above, since at least one detachment preventing engagement portion is provided on each side of the view window, it is possible to prevent the end cap from being accidentally and partly or completely detached from the front end body. Furthermore, if the end cap is cracked, no accidental detachment of the end cap from the front end body tends to occur, so that no mucous membrane is injured by the front end body. Thus, a safe endoscopic operation can be carried out.

FIGS. 5 through 8 show another embodiment of the present invention. In the second embodiment, the shape of the end cap 30 is modified to prevent the end cap from being cracked. In the second embodiment, the elements corresponding to those in FIGS. 1 through 4 are designated with like reference numerals. The main difference of the second embodiment from the first embodiment is the shape of the end cap 30. In addition to the difference in shape, neither the generally V-shaped recess 11 of the front end body 1 nor the projection 33 of the end cap 30 to be fitted in the recess 11 are provided in the second embodiment. A stepped portion 11a which lies in a plane parallel with the axis of the endoscope is provided on the front end surface of the front end body, and the end cap 30 is provided with a stepped portion 33a which engages with the stepped portion 11a of the front end body 1. The stepped portions 11a and 33a prevent the relative rotation between the end cap 30 and the front end body 1 but do not bar the movement of the end cap 30 in the detachment direction, unlike the first embodiment.

Figure 7:
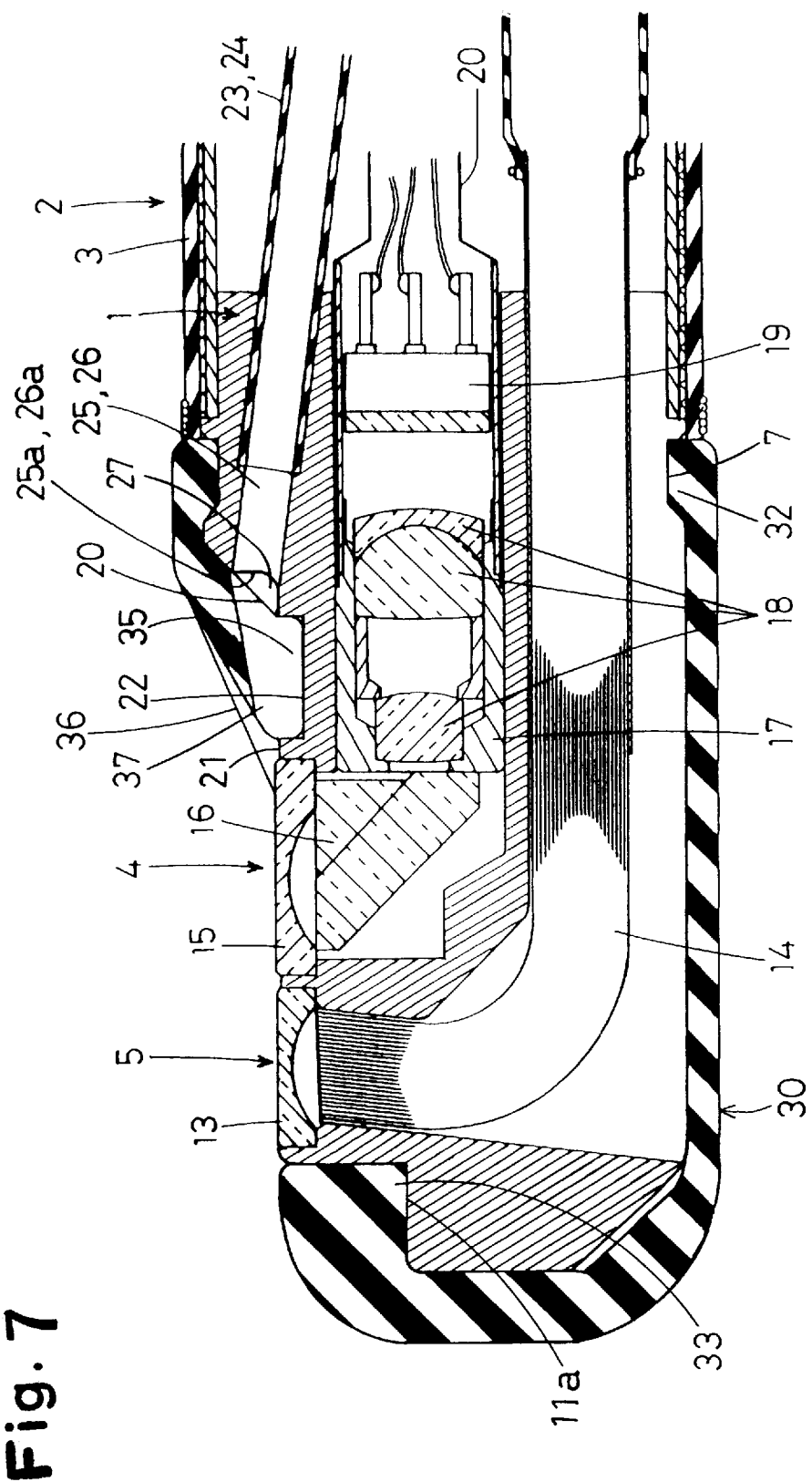
FIG. 7 is a sectional view taken along the line VII—VII in FIG. 6.
Figure 8:
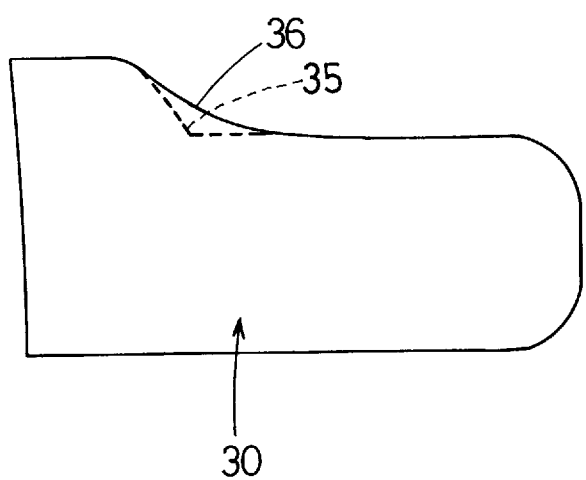
FIG. 8 is a side elevational view of the end cap shown in FIGS. 5 through 7, as viewed in the direction perpendicular to the sheet of the drawing of FIG. 7.

The outer edges of the right and left rear corner portions 36 of the opening 31 of the end cap 30 (i.e., the portions of the end cap 30 that are overlapped on the boundary portion of the rod portion of the front end body 1 with the planar portion 21 thereof) are smoothly rounded so as not to have an angled portion, as viewed in the direction parallel with the planar portion 21, as can be seen in FIGS. 7 and 8. The rounded edge 36 is clearly shown particularly in FIG. 8. Namely, as viewed in the direction parallel with the planar portion 21 when the end cap 30 is attached to the front end body 1, the contour of the rear corner portions of the opening 31 of the end cap 30 is smoothly curved and is located outside the contour of the projection 35 which defines a part of the rear end of the opening 31. The right and left rear corner portions 36 of the opening 31 are located more outward than the surface of the view window 15.

Figure 14:
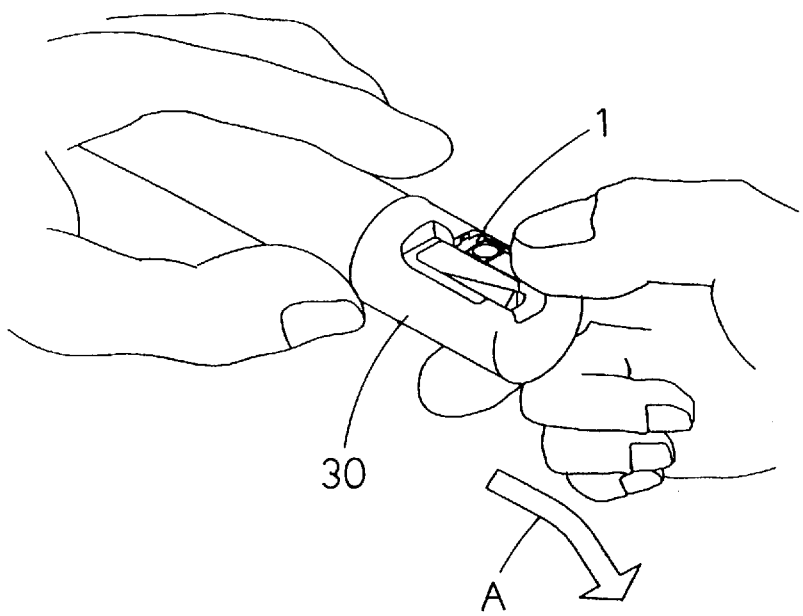
FIG. 14 is a perspective view of a known side-view type endoscope to explain how to detach an end cap from a front end body.
Figure 15:
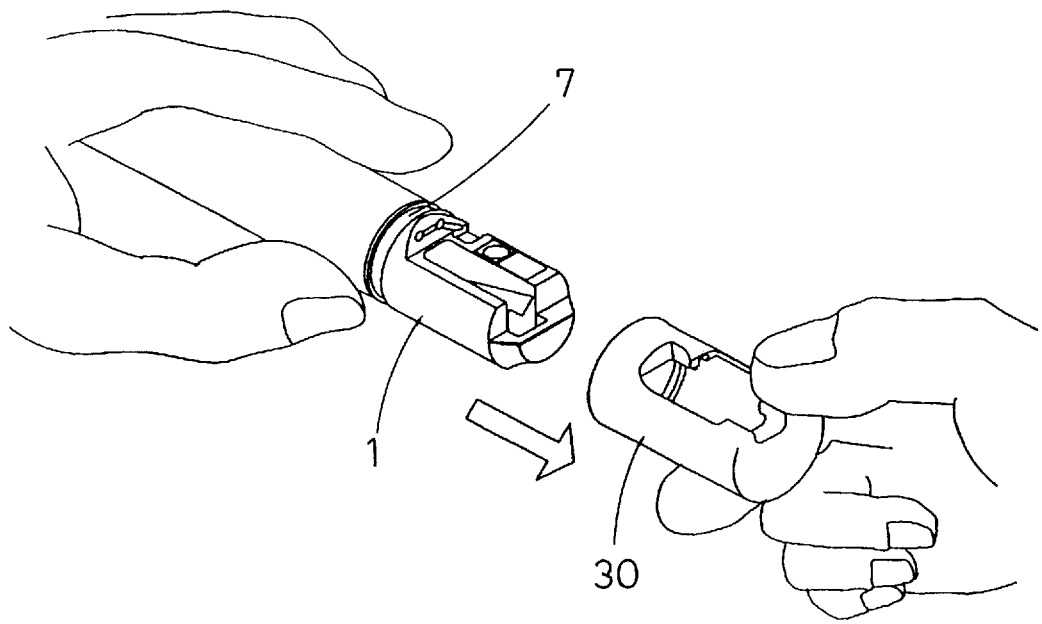
FIG. 15 is a perspective view of a known side-view type endoscope in which an end cap is detached from a front end body; and, FIG. 16 is a perspective view of a known end cap in which cracking has occurred.
Figure 16:
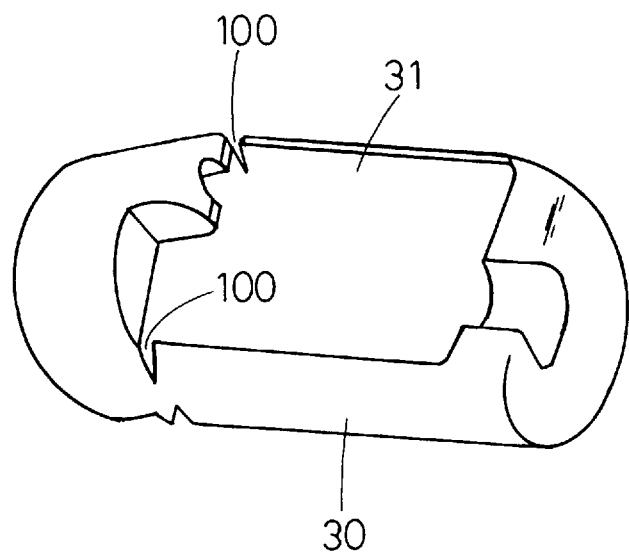

To detach the end cap 30 from the front end body 1, the insertion portion of the endoscope directly behind the rear end of the front end body 1 and the front end of the end cap 30 are held by the fingertips, as shown in FIG. 14. Then the end cap 30 is pulled forward and moved downward to disengage the same from the stepped portion 1a, as indicated by an arrow "A", so that the end cap 30 is partly detached from the front end body 1. In this state, the end cap 30 is pulled further forward and is completely detached from the front end body 1, as shown in FIG. 15.

During the detachment, the rear corner portions 36 of the opening 31 of the end cap 30 at which the stress is concentrated in the prior art are smoothly rounded, and hence, the stress is distributed more evenly. Thus, no cracking due to the stress concentration occurs in the end cap 30.

Consequently, if the end cap is repeatedly attached to or detached from the front end body, or the front end of the insertion portion of the endoscope is moved while the front end of the end cap 30 is strongly pressed against a mucous membrane in the body cavity during an examination using the endoscope, no accidental partial or complete detachment of the end cap 30 from the front end body 1 due to the crack occurs. Thus, there is no fear that the mucous membrane in the body cavity is injured.

Although the right and left corner portions 36 of the opening 31 are located more outward than the surface of the view window 15, the height and shape of the corner portions 36 must be designed so as not to obstruct the field of view.

According to the second embodiment of the present invention, since the edges of the portions of the end cap that are superimposed on the boundary between the rod portion of the front end body and the planar portion thereof are smoothly curved and have no angled portions, as viewed in the direction parallel with the planar portion, the stress is dispersed when the end cap is detached from the front end body. Hence, no crack tends to occur in the resilient end cap when the latter is repeatedly attached to or detached from the front end body, or when a large force is applied to the end cap during an examination using the endoscope. Consequently, the end cap is not accidentally partly or completely detached from the front end body, thus resulting in no injury to the mucous membrane in the body cavity.

Figure 9:
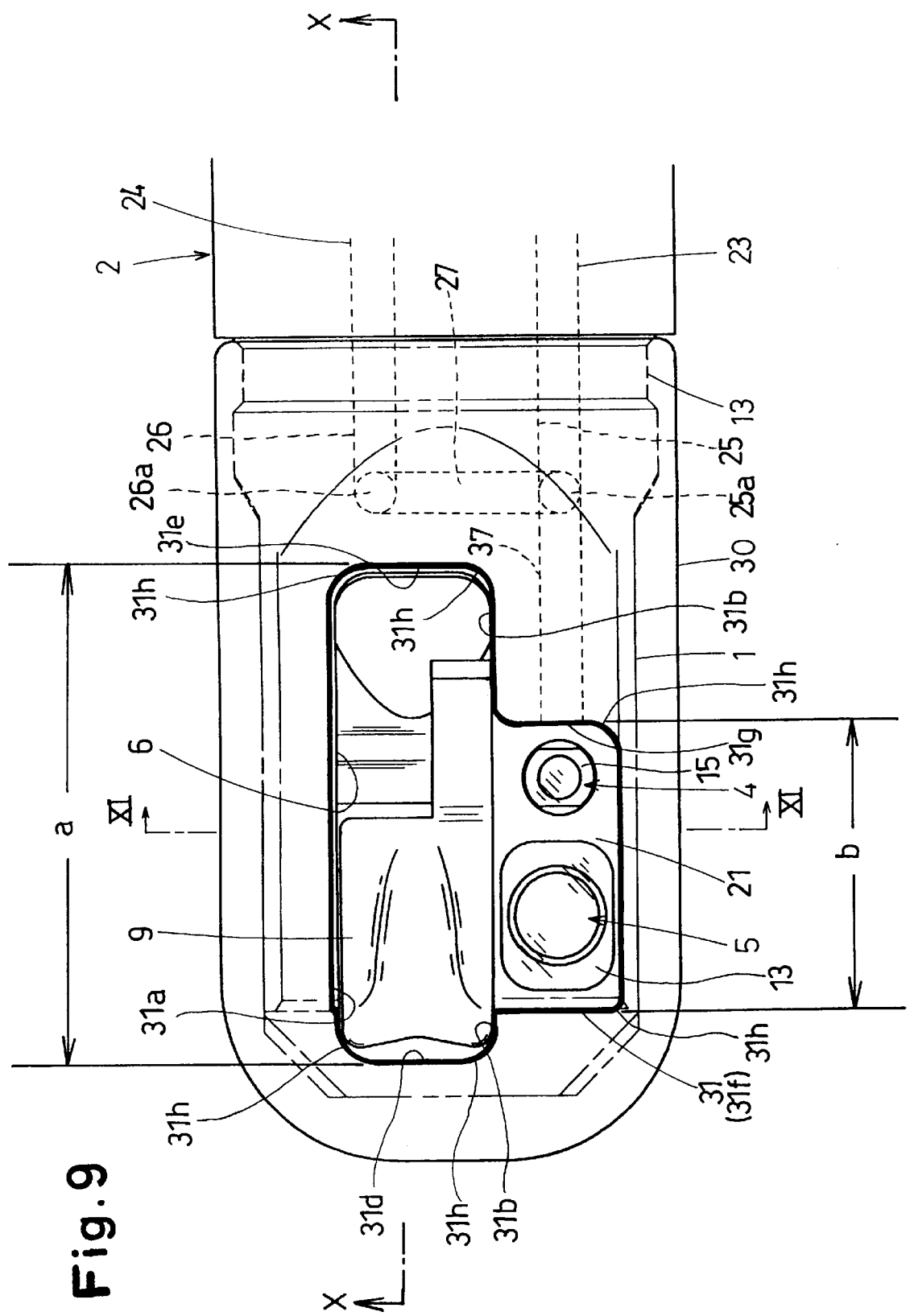
FIG. 9 is a plan view of a side-view type endoscope in which an end cap is attached to a front end body, according to another embodiment of the present invention.
Figure 10:
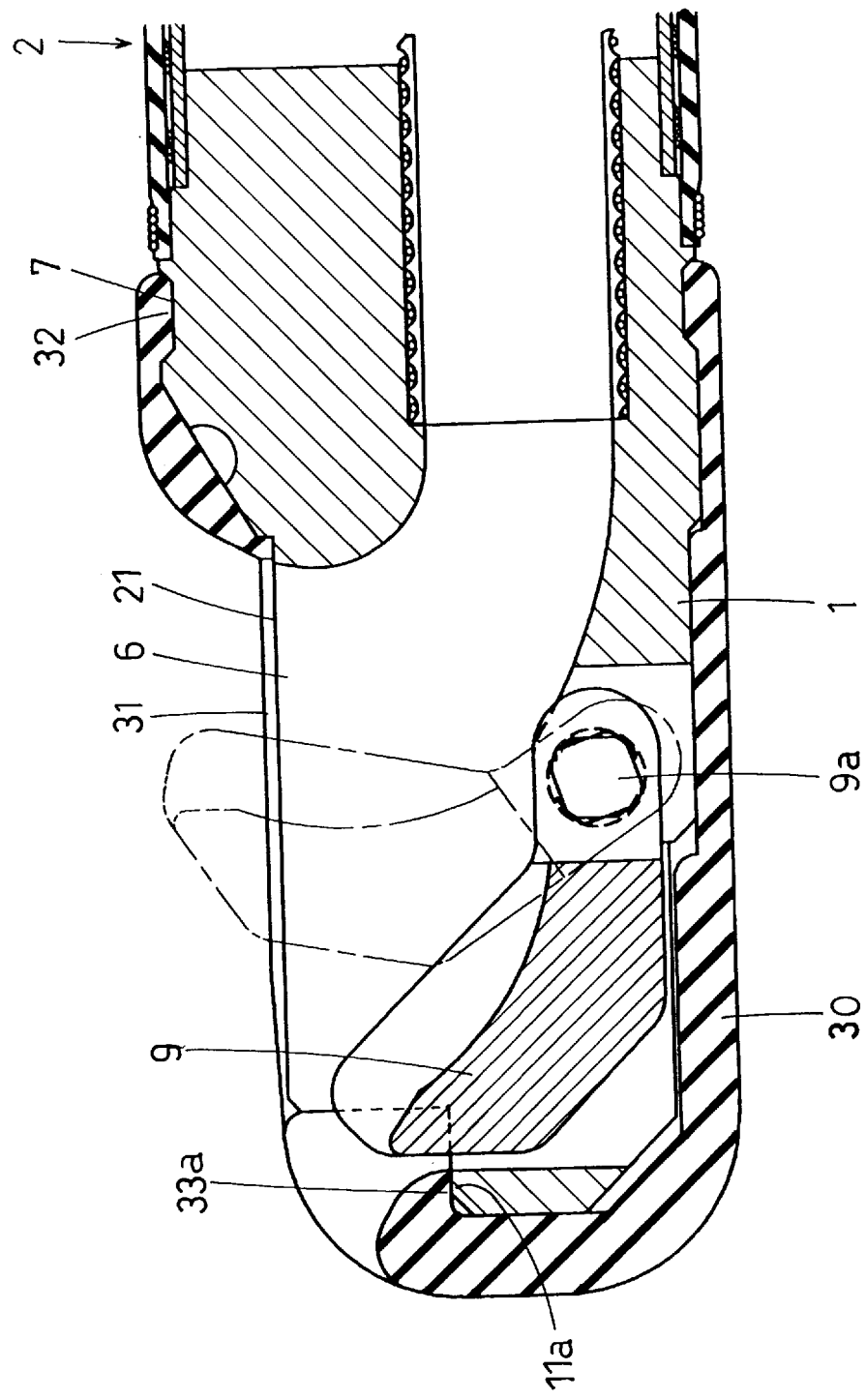
FIG. 10 is a sectional view taken along the line X—X in FIG. 9.
Figure 11:
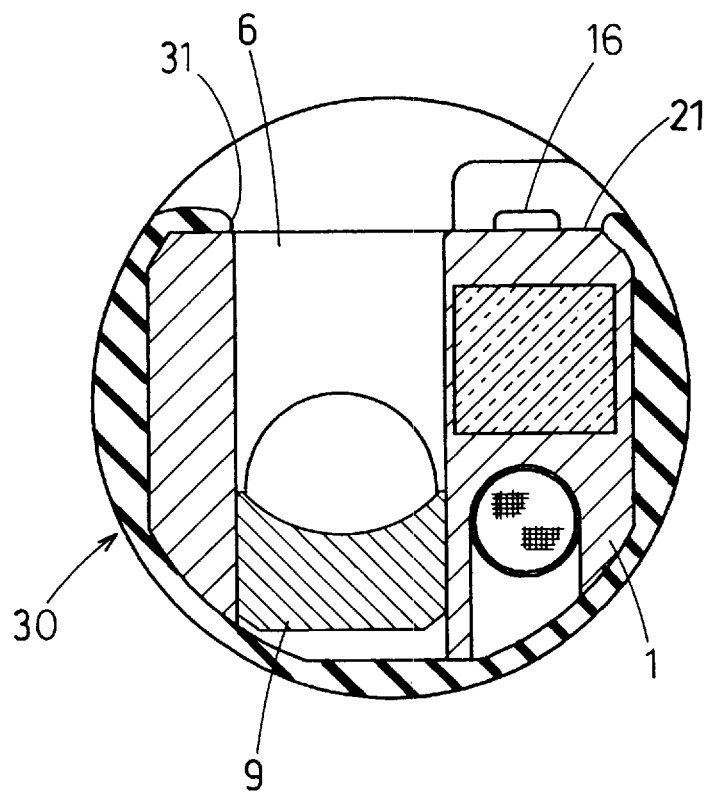
FIG. 11 is a sectional view taken along the line XI—XI in FIG. 9.
Figure 12:
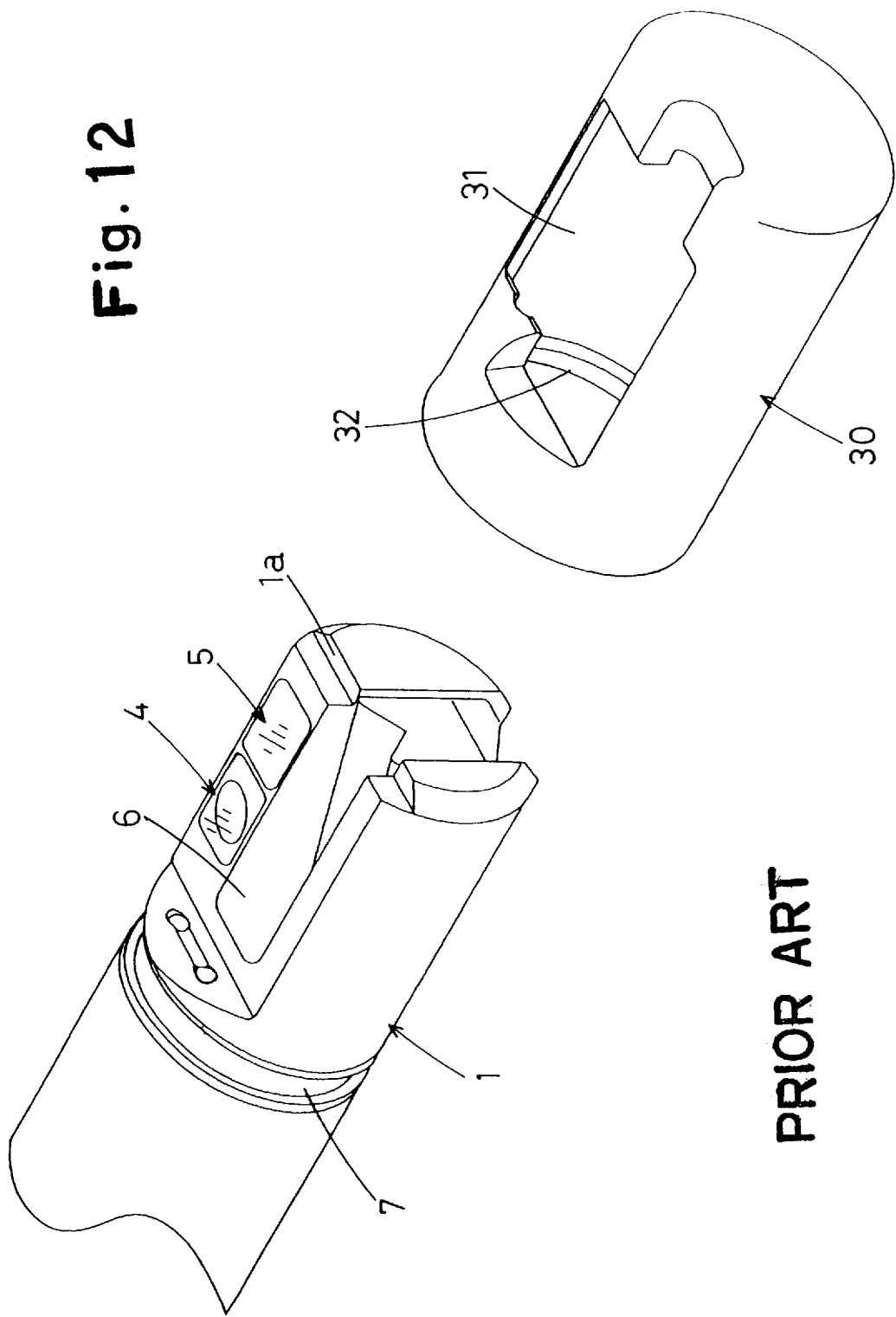
FIG. 12 is a perspective view of a known side-view type endoscope in which an end cap is detached from a front end body.
Figure 13:
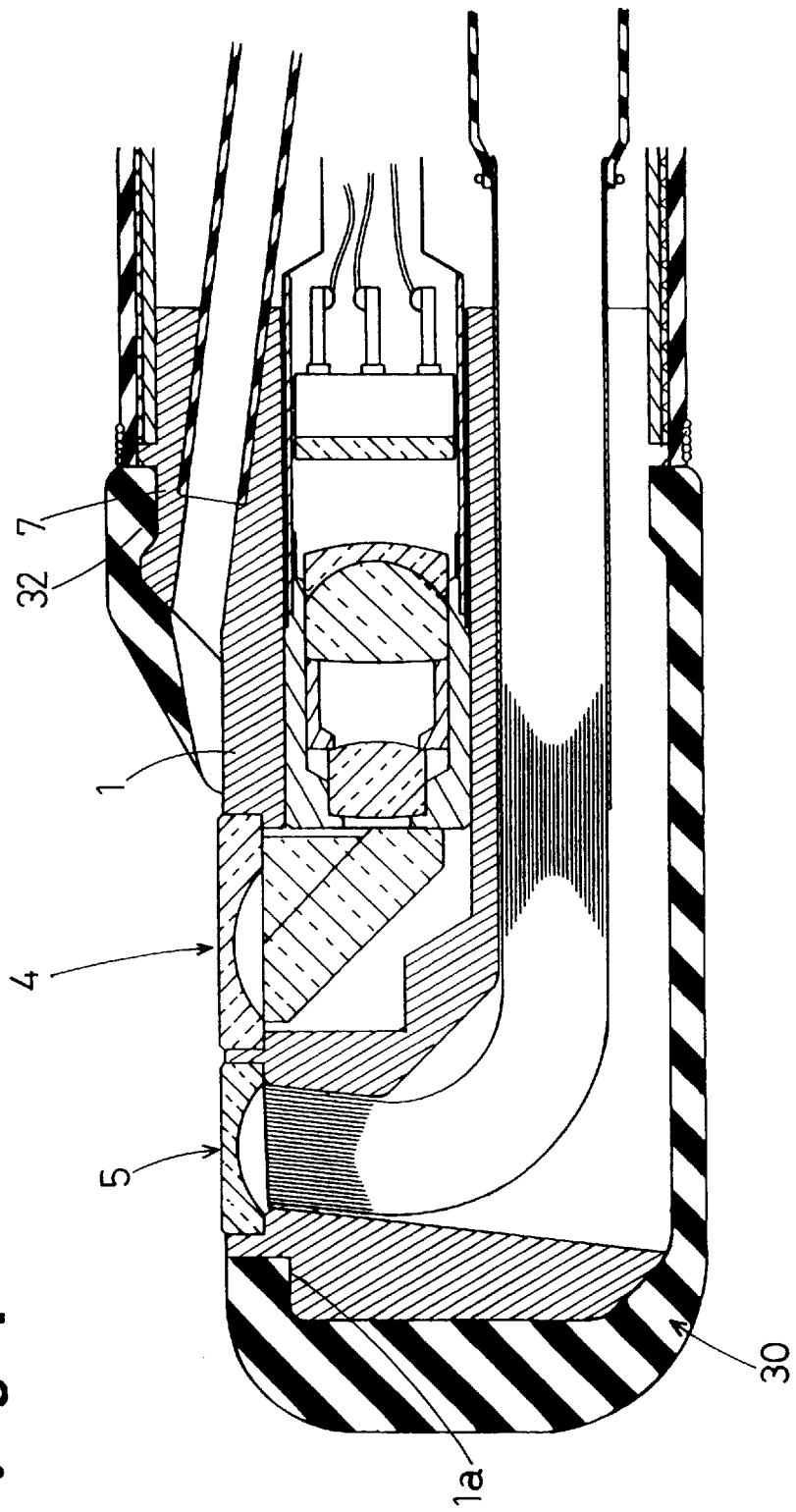
FIG. 13 is a sectional side view of a front end portion of a known side-view type endoscope.

FIGS. 9 through 11 show still another embodiment (third embodiment) of the present invention.

In the third embodiment, the shape of the opening 31 of the end cap 30 is modified so as to prevent the end cap from being easily cracked. In the third embodiment, the elements corresponding to those shown in FIGS. 1 through 4 are designated with like reference numerals. The main difference between the second embodiment and the third embodiment resides in the shape of the opening 31 of the end cap 30.

The opening 31 is provided outside the planar portion 21 of the end cap 30. The shape of the opening 31 is indicated by a thick solid line in FIG. 9. The opening 31 is located as close to the view window 4, the illumination window 5 and the treatment tool insertion opening 6 as possible, without interfering with the function of the view window 4, the illumination window 5, and the treatment tool insertion opening 6. In FIG. 10, 9a designates the center of rotation about which the treatment tool raising piece 9 rotates.

The opening 31 is made as small as possible, provided that the field of view is not restricted, the emission angle of the illumination light can be sufficiently increased, and no interference with the treatment tool raising piece 9 occurs.

Consequently, if an external force is applied to the end cap 30 which is attached to the front end body 1, no deformation of the end cap 30 tends to occur in comparison with the prior art, so that no partial or complete detachment of the end cap from the front end body takes place.

However, if the edge shape of the opening 31 is complicated, it is difficult to produce the end cap and the end cap tends to be broken. To prevent this, the opening 31 is defined chiefly by rectilinear lines which are connected by arcs. Namely, the opening 31 is defined by first and second rectilinear portions 31a and 31b which extend along the side edges of the rectangular treatment tool insertion opening 6 and a third rectilinear portion 31c which extends in parallel with the longitudinal direction of the treatment tool insertion opening 6 and which is located as close to the view window 54 and the illumination window 5 as possible, in the circumferential direction of the end cap 30, and is defined by fourth and fifth rectilinear portions 31d and 31e which extend along the front and rear side edges of the treatment tool insertion opening 6, sixth and seventh rectilinear portions 31f and 31g in the circumferential direction, which connect the second and third rectilinear portions 31b and 31c with the view window 4 and the illumination window 5 being exposed. The parallel rectilinear portions 31a to 31c and the parallel rectilinear portions 31d to 31g are normal to each other and the intersections are smoothly connected by arcs 31h. The distance "a" between the parallel rectilinear portions 31d and 31e is larger than the distance "b" between the parallel rectilinear portions 31f and 31g.

According to the third embodiment of the present invention, since the opening of the end cap which is made of a resilient material and which is attached to the front end body is made as small as possible while ensuring the functions of the view window, the illumination window and the treatment tool insertion opening, of the front end body, when an external force is applied to the end cap, the end cap tends not to deform, and hence, no accidental partial or complete detachment of the end cap from the front end body takes place. Thus, there is no fear that the mucous membrane in the body cavity will be injured by the front end body.

What is claimed is:

1. A front end structure of a side-view type endoscope, comprising:

a front end body which is made from a rigid circular rod;

a planar portion which is formed by partly cutting away said circular rod at the portion other than the rear end thereof, said planar portion being provided with a view window, an illumination window, and a rectangular treatment tool insertion opening; and an end cap made of a resilient material, which is detachably attached to the outer peripheral surface of the front end body, said end cap being provided with an opening located outside the planar portion;

wherein the size of the opening of the end cap is minimized without interfering with the functions of the view window, the illumination window, and the treatment tool insertion opening of the front end body;

and wherein said opening is defined by:

first and second rectilinear portions which extend along the side edges of said rectangular treatment tool insertion opening and a third rectilinear portion which extends in parallel with the longitudinal direction of the treatment tool insertion opening and which is located as close to said view window and said illumination window as possible in the circumferential direction of the end cap; and fourth and fifth rectilinear portions which extend along the front and rear side edges of said rectangular treatment tool insertion opening, and sixth and seventh rectilinear portions in the circumferential direction, said sixth and seventh rectilinear portions connecting said second and third rectilinear portions with the view window and the illumination window being exposed;

wherein said first, second and third parallel rectilinear portions and said fourth, fifth, sixth and seventh parallel rectilinear portions are normal to each other and their intersections are smoothly connected by arcs.

2. The front end structure of a side-view type endoscope according to claim 1, further comprising a treatment tool raising piece which is provided in said treatment tool insertion opening so as to move in accordance with a remote-control operation, said opening of the end cap being made as small as possible so as not to interfere with the treatment tool raising piece.

3. The front end structure of a side-view type endoscope according to claim 1, wherein the opening of the end cap is made as small as possible without reducing the field of view of the endoscope or reducing the emission angle of illumination light emitted from said illumination window.

4. The front end structure of a side-view type endoscope according to claim 1, the distance between said fourth and fifth parallel rectilinear portions being larger than the distance between said parallel sixth and seventh rectilinear portions.

5. A front end structure of a side-view type endoscope, comprising:

a metal front end body which is made of a circular rod;

a planar portion which is formed by partly cutting away said circular rod at the portion other than the rear end thereof, said planar portion being provided with a view window, an illumination window, and a treatment tool insertion opening; and an end cap made of a resilient material, which is detachably attached to the outer peripheral surface of the front end body, said end cap being provided with an opening located outside the planar portion;

wherein the outer edge of the portion of the end cap that is overlapped on a boundary between the circular rod portion of the front end body and the planar portion thereof is smoothly rounded without having an angled portion; and wherein the rear right and left corner portions of the opening of the end cap are smoothly rounded without having angled portions.

6. The front end structure of a side-view type endoscope according to claim 5, wherein the front end body is provided with a recess at the rear end of the planar portion on which the view window is formed, and wherein said end cap is provided with an engagement projection which is engaged in the recess, the contour of the opposite sides of the opening of the end cap at the rear end thereof is located more outward than the contour of the portion of the end cap on which the engagement projection is provided, as viewed in the direction parallel with the planar portion.

7. The front end structure of a side-view type endoscope according to claim 6, wherein the contour of the opposite sides of the rear end of the opening of the end cap is located more outward than the surface of the view window formed on the planar portion.

* * * * *